United States Patent [19]

Leprevost

[11] Patent Number: 4,693,236
[45] Date of Patent: Sep. 15, 1987

[54] CLOSURE APPLIANCE FOR USE IN CONNECTION WITH SURGICAL OSTOMY

[76] Inventor: Leonardo Leprevost, Pasaje Maluquer, 9 Barcelona, Spain

[21] Appl. No.: 834,515

[22] Filed: Feb. 28, 1986

Related U.S. Application Data

[63] Continuation of Ser. No. 617,538, Jun. 5, 1984, abandoned.

[30] Foreign Application Priority Data

Jun. 9, 1983 [ES] Spain ................................. 272.994
Nov. 9, 1983 [ES] Spain ................................. 275.834
Feb. 27, 1984 [ES] Spain ................................. 277.753

[51] Int. Cl.$^4$ ............................................. A61B 19/00
[52] U.S. Cl. ........................... 128/1 R; 128/DIG. 25; 604/333; 604/337
[58] Field of Search ............................. 604/332–345; 128/1 R, DIG. 25

[56] References Cited

U.S. PATENT DOCUMENTS 4,121,589 10/1978 McDonnell ........................ 604/337
4,534,760 8/1985 Raible ............................ 604/338 X

FOREIGN PATENT DOCUMENTS 2648222 4/1978 Fed. Rep. of Germany ...... 604/332
2740682 3/1979 Fed. Rep. of Germany ...... 604/337
3011742 10/1981 Fed. Rep. of Germany ...... 604/332
0274978 4/1981 Spain .
2007983 5/1979 United Kingdom ................ 604/337

Primary Examiner—William R. Dixon, Jr.
Assistant Examiner—Karl Group
Attorney, Agent, or Firm—Birch, Stewart, Kolasch & Birch

[57] ABSTRACT

A closure appliance for use in surgical ostomy comprising an upper member and a lower member. The upper member contains a cavity for receiving a closure. The closure is provided with filtration and absorbent materials. The lower member contains a plurality of tubular passageways which communicate with the cavity in the upper portion. Magnetic members surround the tubular passageways for magnetically securing the device to a magnetized annulus which has been implanted in the surrounding skin of the stoma. The closure appliance is utilized to tightly fit within the stoma and to selectively permit the evacuation of fluids from the interior of the stoma.

17 Claims, 8 Drawing Figures

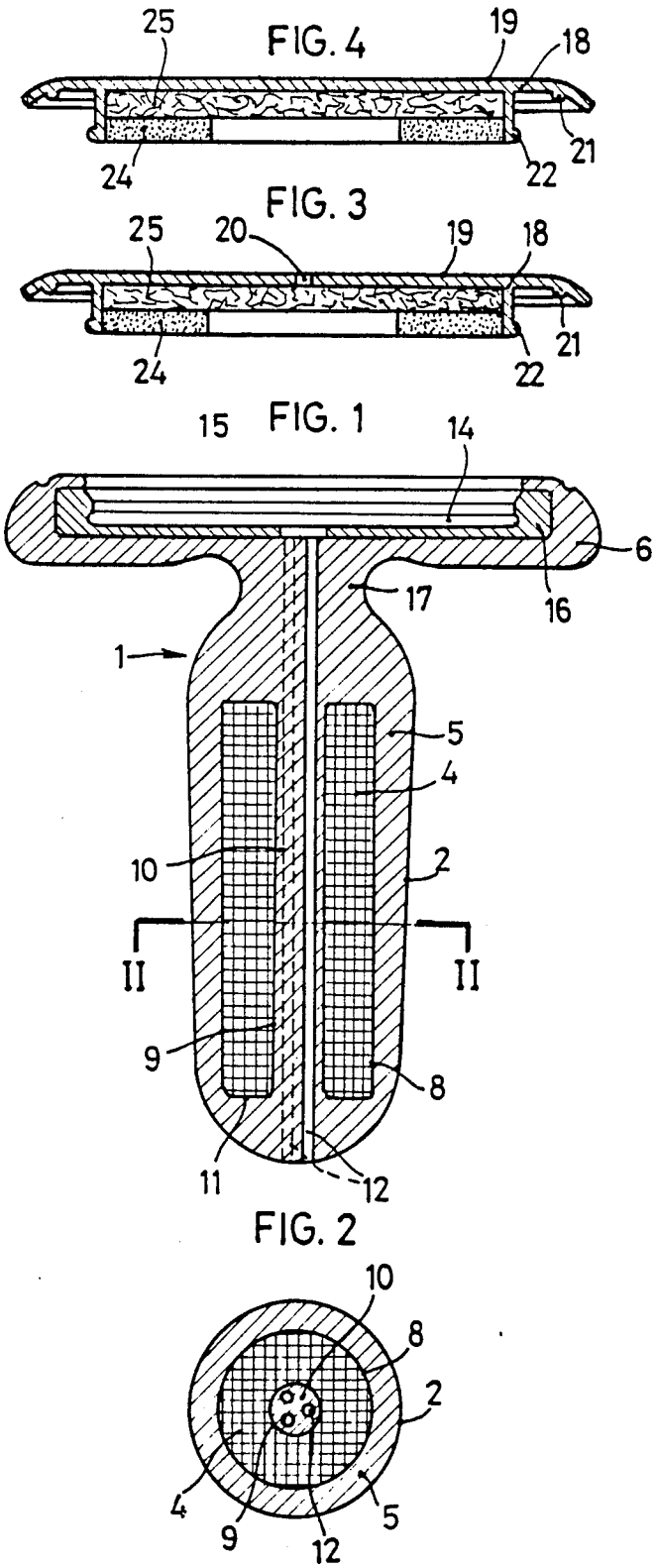

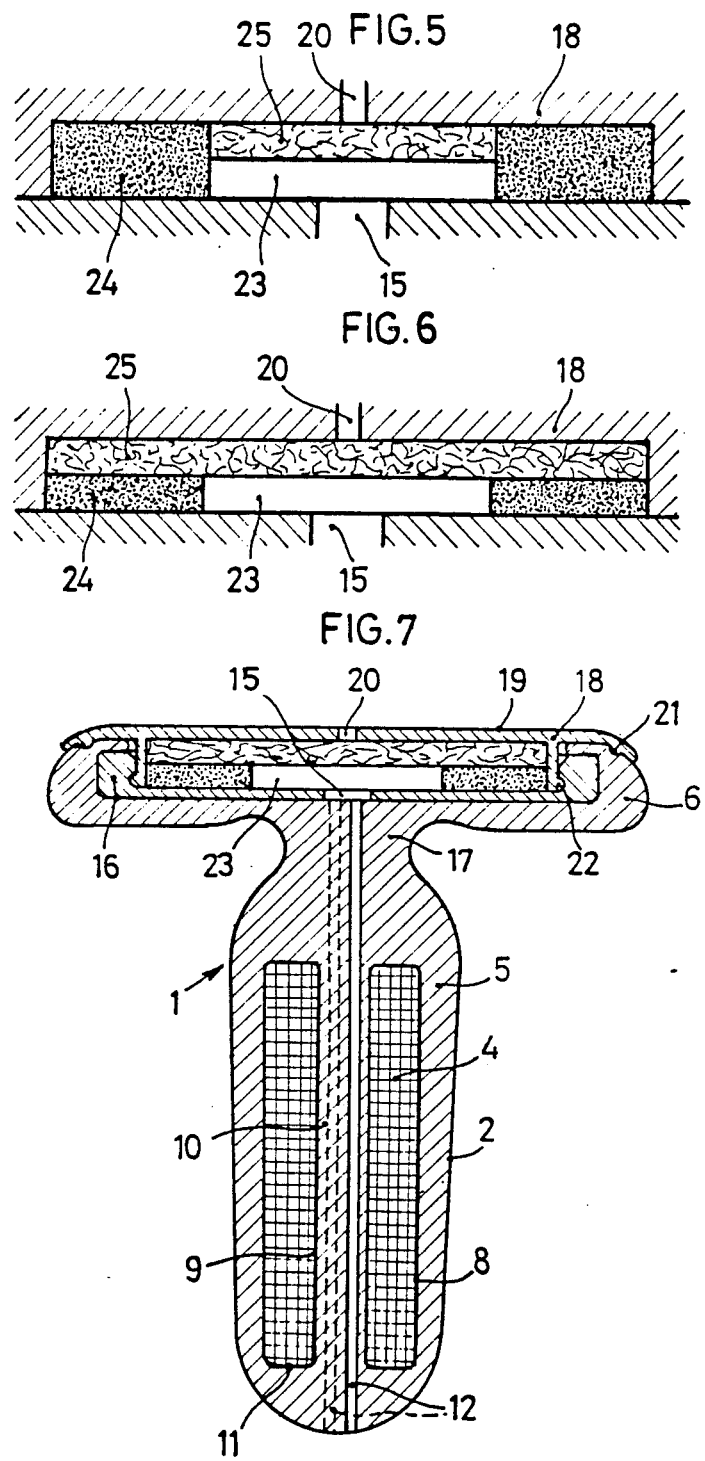

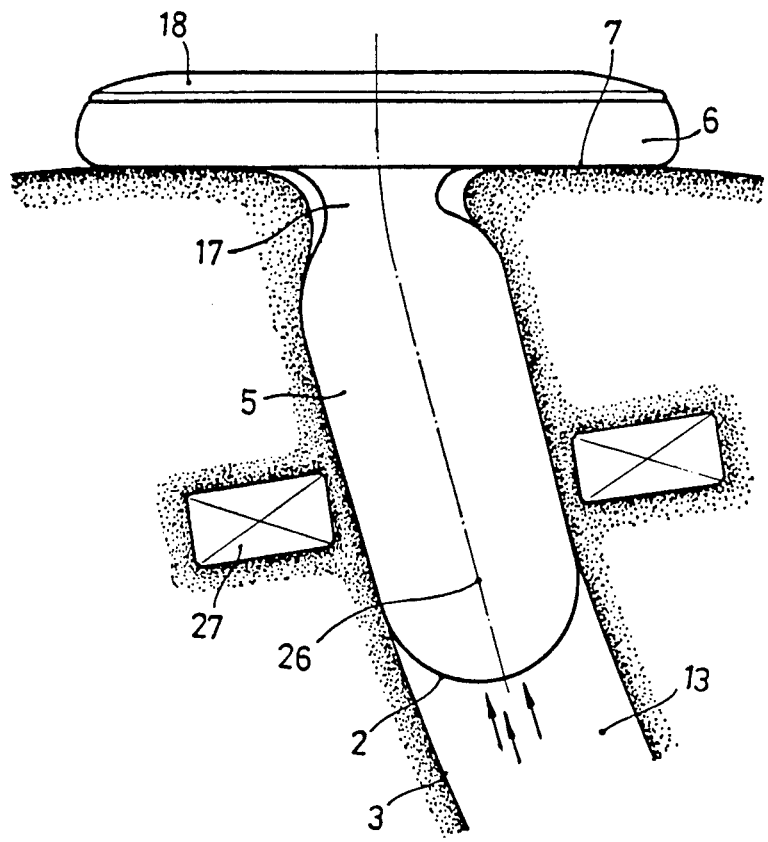

CLOSURE APPLIANCE FOR USE IN CONNECTION WITH SURGICAL OSTOMY

This application is a continuation of application Ser. No. 617,538 filed on June 5, 1984, now abandoned.

BACKGROUND AND SUMMARY OF THE INVENTION

The present invention is directed to a closure appliance for use in connection with surgical ostomy and which, by virtue of its particular shape and structure, offers considerable improvements as compared to the currently available appliances.

The problems normally arising with ostomy closure appliances at present, especially in cases of abdominal colostomy, relate to the sealing action of the stoma. In fact the majority of the appliances employed for sealing the stoma comprise a magnetic ring which is located as a fitting around the stoma tube and implanted in the proximity of the patient's skin such that it holds the actual closure member in place by means of the magnetic attraction between the ring and one or more magnetic nuclei provided in the closure member. These closure members generally consist of a body situated on the outside of the stoma rigidly attached to another body which is inserted into the interior of the stoma. The outer body has incorporated therein magnetic elements which due to the magnetic attraction existing between these elements and the implanted ring, cause the closure of the stoma. This action can be enhanced by further magnetic elements located in the interior body.

Use of appliances as described above gives rise to problems with respect to the sealing effectiveness of the closure in view of the fact that the magnetic attractive force between the magnetic ring whih has been implanted in the patient and the magnetic nuclei which are located within the closure component varies as a function of the relative distance between them. This distance is subject to variations over a period of time, given that the patient's morphology is subject to evolution, virtually never remaining stable, with an increase or a decrease in the adipose tissue or the layer separating the implanted ring and the surface of the skin on which the closure appliance has been fitted. This gives rise to serious inconveniences with the increase or decrease of the distance resulting in a change in the mutually attractive forces and hence an adverse change in the sealing action of the closure appliance.

These inconveniences were disclosed in the Spanish Utility Model No. 274,978 and a solution was put forward in this patent, in the form of a movable magnetic element in the body of the closure appliance which is fitted in the interior of the stoma and which in some manner permitted the magnetic force between the implanted ring and the closure appliance to be varied.

On other occasions experiments have demonstrated that the rigidity of the closure appliances frustrates a solution to the problem of sealing by not allowing a satisfactory adaptation to the stoma. This problem is compounded by the positioning of the member to be inserted in the patient in that it is difficult to ensure the parallelism between the inserted member and the abdominal surface and thus the relative position of the insert may vary with the posture of the patient thus producing an angularity of the closure device relative to the abdomen and thus opening a passage of incontinency for liquids and solids.

The appliance which is the object of the present invention provides a solution to the disadvantages described above in that it comprises a closure device consisting of a component made in a highly flexible material such as silicone and of which the lower member, designed to be inserted within the stoma has disposed therein a magnetic element and a plurality of tubes permitting the exhaustion of fluids from inside the stoma. These tubes open into a cavity in an upper member, there being housed within the cavity an absorbent material and another filtration material which respectively absorb and filter the liquids and gases which arrive in the cavity proceeding from the interior of the stoma.

The upper member may incorporate preferably an element of greater consistency, providing greater rigidity in that member. In addition the upper member may be fitted with a detachable cover.

Experiments carried out by the applicant have demonstrated that the elasticity of the material of which the appliance is made, together with the rotula effect resulting from the flexible and elastic joint uniting the interior and exterior members result in a perfect adaptation of the stoma wall to the lower or internal member of the appliance and hence a hermetic and watertight seal of the stoma.

The above considerations have led the applicant to include in the design a plurality of tubes for the evacuation of the fluids from the lower member of the appliance. To achieve this the magnetic element which is housed within the interior of the lower member of the appliance is provided with a central orifice and the lower member has an internal void shaped to conform to the shape of the magnetic element. The central orifice in the magnetic element has located within it a stem in which there is a plurality of passageways providing for the outlet of fluids from the interior of the stoma, through the full length of the lower member of the appliance to the cavity provided in the upper member of the appliance.

Equally it has been demonstrated that the continual evacuation of the gases emanating from the stoma together with the presence of mucous in the colon result in the need to change, at frequent intervals, the filters and the absorbent material which has been provided in the outer member of the closure appliance. This consideration has led to the arrangement which allows for the provision, in the applicant's design, of an easily detachable cover of a material suitable for discarding and which, in turn, incorporates the elements required for the filtration of the gases and the absorption of liquids. The cover can be readily replaced by the patient with a new one when this becomes necessary.

According to the present applications there is the provision for the patient to fix to the external member either a detachable cover which incorporates an orifice allowing the escape of gases to the exterior or alternatively a cover which provides a tight seal without the use of orifices such that the patient, at his option, may use one or the other alternatives in accordance with the needs of his daily routine, that is, as to whether he wishes to allow the escape of the gases from the stoma, or not.

The cover without the orifices permits the patient to ensure that the stoma is isolated from the outside when, for example, he is bathing and thus desires to prevent the penetration of water into its interior.

In one preferred embodiment, the detachable cover has incorporated therein the filtration material for the gases as well as the absorbent material for the liquids which emanate from the stoma and is preferably made of a throw-away material for a one-time use only. This facilitates the handling of the cover and the replacement of the cover by the user-patient.

A further feature of the present application is the provision in the cover of the void which communicates downwardly with the tube coming from the stoma such that it is surrounded laterally by the absorbent element and is closed at its upper face by the filter material. This arrangement facilitates the collection of gases and liquids, allowing the liquids and gases to flow from the stoma into the void as they emerge from the former. The liquids are then absorbed by the absorbent walls and the gases pass through the upper filtration material so that they may then pass to the exterior through the orifices provided in the upper portion of the cover.

This arrangement, providing for the separate evacuation of the gases and the liquids, prevents the combination of some of the liquid with the flow of gases and hence avoids a possible blockage of the filter material.

The structure of the absorbent and filtration materials may take the form either of an annulus of absorbent material on which is placed a disc of the filtration material having the same external diameter as the former or of an annulus of absorbent material with the filtration material housed in the central zone of the said annulus.

The cover is completed by providing means for its attachment to the ostomy closure appliance and also the incorporation in its upper part of means for allowing a visual estimation of the percentage of absorbed product in the absorbent material, as for example, a device which indicates by a colour change the degree of humidity in the absorbent material.

This closure appliance, upon being fitted into the stoma, following implantation of the magnetic ring, will ensure that the exterior member will remain adapted to the mouth of the stoma and hence close it, and will permanently maintain itself in that position by virtue of the magnetic mutual attraction between the implanted ring and the magnetic element housed within the interior member of the closure appliance. Also in view of the flexibility of the union between the interior member and the exterior member, the interior member is free to move angularly with respect to the exterior member in a rotula movement, and as a consequence, the angle of the stoma axis with respect to the magnetic element embedded in the inner member, corrects itself for a lack of perpendicularity in the appliance by seeking the position of least magnetic reluctance, thus providing a correct operation of the closure characteristic of the appliance.

For a better understanding of the general characteristics of the ostomy closure appliance of the present invention, there are attached to this specification, descriptive drawings illustrating one practical embodiment of the same in accordance with the principles recited in the claims but with the observation that the sketches as drawn must be interpreted in their most general sense without implying any restrictive character in any form.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIG. 1 shows a cross-sectional view of the appliance of the present invention;

FIG. 2 is a section taken through line 11—11 in FIG. 1 in which can be seen the outlet tubes for the evacuation of gases and fluids.

FIGS. 3 and 4 show sectional views of the two covers, one provided with orifices and the other not so provided. Either one of the covers can be fitted to this appliance;

FIG. 5 shows a detail of the devices for filtration and absorbation located in the cover;

FIG. 6 shows a view of an alternative arrangement of FIG. 5 in which the filter element consists of a disc which extends over the ring that forms the absorbent material;

FIG. 7 shows a sectional view of the appliance of the present invention, fitted with a detachable cover provided with orifices; and FIG. 8 is a schematic view of the appliance of the present invention fitted to a surgical opening of the ostomy type in which may be seen the arrangement and fitting of the appliance when the axis of the stoma is not perpendicular to the abdominal plane.

To assist in interpreting the various members of the appliance the description below carries reference numbers corresponding to those on the attached drawings.

The drawings portray a closure appliance comprising a body -1- made of a highly elastic material, such as silicone, which is adapted to be lodged in the interior of the surgical opening where the flexible surface -2- remains firmly adhered to the walls -3- of the stoma. A magnetic element -4- is incorporated into a lower member -5- which is connected through a flexible union to an upper member -6- which is adapted to lie on the outside of the stoma and adapt itself to the mouth -7- of the stoma.

The magnetic element -4- has a shape coincident with that of the cavity -8- of the lower member -5- of the appliance, in which it is lodged. A central orifice -9- is provided in which there is disposed a stem -10- made of an elastic material, this being a prolongation of the bottom extremity -11- of the cavity -8- and through which are provided a plurality of tubular passageways -12- for the evacuation of fluids from the interior of the stoma -13- in the direction of the cavity -14- in the upper member -6- of the appliance. The fluids pass through the orifice -15- in component -16- which is located in the said cavity -14- for the purpose of providing greater rigidity to the upper member -6-.

The passage between the interior of the stoma -13- and the outside may be by any other suitable means, such for example as by lateral channels in the internal member -5- as well as, in the magnetic element -4-.

The flexible joint between the members -5- and -6- is illustrated in the embodiment shown in the drawings, in the form of a stem or neck -17- which is a prolongation of the member -5- and which expands into the flattened section -8- which in turn rests against the mouth -7- of the stoma. This stem permits angular movement between the members -5- and -6- by way of a rotula action.

The body -1- may alternatively consist of two separate members, one interior and the other exterior, mutually joined by means of an intermediate flexible union such that the two members are free to move angularly with respect to each other with the same rotula action as above.

As the drawings illustrate, the external member -6- is fitted with a cover -18- consisting of a dish shaped piece made preferably in of a disposable material and having an upper zone -19- in which there is an orifice -20-, with flange means for its attachment to the said upper part -6- of the appliance 1. These flanges -21- and -22- fit into corresponding grooves in the closure appliance and in the component -16-. The lower side of the cover takes the form of a dish which defines a void -23- and in which are housed the absorbent material for liquids and the filter material for the gases.

As shown in the FIGS. 5 and 6, the arrangement of the absorbent and filtration components -24- and -25- respectively, in the void -23- is such that the void -23- is defined as to its upper boundary by the filtration material and laterally by the absorbent material in such a manner that the liquids coming from the stoma can easily be absorbed by the absorbent material -24- while the gases pass through the filter material -25- and out to the exterior via the orifice -20- in the cover.

According to the particular requirements, the patient may attach to the appliance either the detachable cover provided with orifices -20-, for permitting the escape of gases to the exterior, or alternatively the cover can exclude the presence of an orifice, thus ensuring a sealed closure to the surgical opening. These two optional covers are shown in FIGS. 3 and 4 respectively.

The appliance as described above, with its flexible union allows an angular variation between the lower member -5- and the upper member -6- when there is an angular change between the axis of the tube -26- and the closure appliance, while permitting a correct functioning of the magnetic element -4- and the magnetized annulus -27- which has been implanted in the patient, these elements operating in the position of minimum magnetic reluctance.

The appliance as described can be applied to all types of ostomy conditions, both colostomy and ileostomy in that it is effective under correct conditions both for the retention of all types of solids and fluids, be they abdominal or perineal.

It should be noted that the detachable cover which is fitted to the outer body -6- may have incorporated therein a bag for the collection of liquids, this bag not being shown in the drawings.

I claim:

1. A closure appliance for use in cases involving surgical ostomy which comprises
    a body formed by an upper member adapted to be disposed on the outside of the stoma and a lower member adapted to extend inside the stoma, said upper and lower members being securely joined together by an intermediate area of reduced cross section forming a flexible, elastic joint which allows relative angular movement between said members in a rotula manner,
    a first magnetic element incorporated in the wall of said lower member, in such a manner as to be capable of interacting with a second magnetic element surrounding the stoma so as to cause the lower member wall to form a seal with the stoma wall, and
    at least one passageway extending through said body and providing communication between the upper member and the bottom of the lower member, said upper member containing a cavity which communicates with the interior of the stoma through said passageway extending through the lower member of the appliance.

2. The closure appliance of claim 1 wherein a plurality of tubular passageways extend axially from the cavity in the upper member to the bottom of the lower member.

3. The closure appliance of claim 1 wherein the flexible elastic joint is in the form of a flexible elastic stem.

4. The closure appliance of claim 1 wherein the cavity in the upper member is provided with a detachable cover, said cavity containing means for filtering and absorbing the emanations proceeding from the stoma.

5. The closure appliance of claim 1 wherein the first magnetic element surrounds said passageway.

6. The closure appliance of claim 2 wherein a stem of elastic material is disposed within the first magnetic element which surrounds said passageways, said passageways extending through said elastic material from the cavity in the upper member to the bottom of the lower member for the evacuation of fluids from the interior of the stoma to the cavity in the upper member.

7. The closure appliance of claim 1 wherein the cavity in the upper member contains a component which conforms thereto, thereby providing a greater rigidity to said upper member, said component containing an orifice which is coincident with the position of the passageway to permit the evacuation of fluids from the interior of the stoma.

8. The closure appliance of claim 4 wherein the detachable cover contains said filtering and absorbing means.

9. The closure appliance of claim 8 wherein the detachable cover contains at least one hole so that gases emanating from the stoma can flow through the hole to the outside of the device.

10. The closure appliance of claim 9 wherein the detachable cover is in the form of a disk and the filtering means and absorbing means disposed therein define a cap chamber which communicates with the fluids emanating from inside of the stoma.

11. The closure appliance of claim 10 wherein the filter material covers the inside of the cap and the absorbent material laterally surrounds the cap chamber, said cap chamber thereby being defined laterally by the walls of the absorbent material and at the top by the filter material.

12. The closure appliance of claim 10 wherein the detachable cover is provided with means for facilitating its attachment to the closure appliance.

13. The closure appliance of claim 10 wherein the detachable cover is provided with a transparent zone for viewing changes of color in the absorbent material arising from changes in the level of humidity in the absorbent material.

14. The closure appliance of claim 4 wherein the detachable cover is free of holes and thus provides a tight seal construction.

15. The closure appliance of claim 4 wherein the detachable cover is fitted with a bag for the collection of fluids.

16. The closure appliance of claim 1 wherein said intermediate area of reduced cross-section is substantially perpendicular to the longitudinal axis of the closure appliance, in its relaxed state.

17. A closure appliance for use in cases involving surgical ostomy which comprises a magnetic ring adapted to be implanted in a patient in the surrounding skin of a stoma, a body formed by an upper member adapted to be disposed on the outside of the stoma and a lower member adapted to extend inside the stoma, said upper and lower members being securely joined together by an intermediate area of reduced cross section forming a flexible, elastic joint which allows relative angular movement between said two members in a rotula manner, a magnetic element incorporated in the wall of said lower member, which interacts with said magnetic ring to cause a seal to form between the stoma and the lower member wall and at least one passageway extending through said body and providing communication between the upper member and the bottom of the lower member, said upper member containing a cavity which communicates with the interior of the stoma through said passageway extending through the lower member of the appliance, whereby the lower member of the body is tightly secured within the stoma to selectively permit the evacuation of fluids from the interior of the stoma.

* * * * *